United States Patent
Audousset et al.

(10) Patent No.: US 7,442,215 B2
(45) Date of Patent: Oct. 28, 2008

(54) PROCESS FOR COLORING KERATIN FIBERS COMPRISING TREATING THE SCALP WITH AT LEAST ONE SORBITAN ESTER

(75) Inventors: Marie-Pascale Audousset, Asnieres (FR); Christine Rondeau, Sartrouville (FR)

(73) Assignee: L'Oreal S.A., Paris (FR)

( * ) Notice: Subject to any disclaimer, the term of this patent is extended or adjusted under 35 U.S.C. 154(b) by 271 days.

(21) Appl. No.: 11/502,406

(22) Filed: Aug. 11, 2006

(65) Prior Publication Data

US 2008/0216254 A1    Sep. 11, 2008

Related U.S. Application Data

(60) Provisional application No. 60/748,206, filed on Dec. 8, 2005.

(30) Foreign Application Priority Data

Aug. 11, 2005   (FR)   .................................. 05 52494

(51) Int. Cl.
*A61Q 5/10* (2006.01)
(52) U.S. Cl. ........................ 8/405; 8/406; 8/410; 8/411; 8/421; 8/435; 8/580; 132/202; 132/208
(58) Field of Classification Search .................... 8/405, 8/406, 410, 411, 421, 435, 580; 132/202, 132/208
See application file for complete search history.

(56) References Cited

U.S. PATENT DOCUMENTS

| | | | |
|---|---|---|---|
| 4,003,699 A | 1/1977 | Rose et al. | |
| RE30,199 E | 1/1980 | Rose et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Löwe et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,730,789 B1 | 5/2004 | Birault et al. | |
| 2002/0050013 A1 | 5/2002 | Vidal et al. | |
| 2003/0019051 A9 | 1/2003 | Vidal et al. | |

FOREIGN PATENT DOCUMENTS

| | | |
|---|---|---|
| DE | 23 59 399 | 6/1975 |
| DE | 38 43 892 A1 | 6/1990 |
| DE | 41 33 957 A1 | 4/1993 |
| DE | 195 43 988 A1 | 5/1997 |
| DE | 199 23 438 A1 | 11/2000 |
| EP | 0 770 375 B1 | 5/1997 |
| FR | 2 733 749 A1 | 11/1996 |
| FR | 2 750 048 A1 | 12/1997 |
| FR | 2 801 308 A1 | 5/2001 |
| GB | 1 026 978 | 4/1966 |
| GB | 1 153 196 | 5/1969 |
| JP | 2-19576 | 1/1990 |
| WO | WO 94/08969 | 4/1994 |
| WO | WO 94/08970 | 4/1994 |
| WO | WO 96/15765 | 5/1996 |
| WO | WO 2004/093835 A1 | 11/2004 |

OTHER PUBLICATIONS

Hydrophobic oxidative hair dye-XP-002380394 (Feb. 2002).*
Patent Abstracts of Japan, vol. 015, No. 388, Oct. 2, 1991, JP 03 157320 A.
"Hydrophobic Oxidative Hair Dye 8781-58," Haircareformulation.com, Feb. 11, 2002, XP-002380394.
English language abstract of DE 199 23 438 A1, Nov. 30, 2000.
French Search Report for FR 0552494, dated May 10, 2006, Examiner E. Siatou.
French Search Report for FR 0552492, dated May 11, 2006, Examiner E. Siatou, for co-pending patent application, filed Aug. 11, 2006.
Co-pending Patent Application— Title: Composition for Dyeing Keratin Fibers Comprising at Least One Oxidation Base and a Polyoxyethylenated Sorbitan Ester Filed: Aug. 11, 2006.
English language abstract of EP 0 770 375 B1, May 2, 1997.
English language abstract of JP 2-19576, Jan. 23, 1990.

* cited by examiner

*Primary Examiner*—Eisa B Elhilo
(74) *Attorney, Agent, or Firm*—Finnegan, Henderson, Farabow, Garrett & Dunner L.L.P.

(57) ABSTRACT

Disclosed herein is a process for dyeing keratin fibers such as the hair, comprising, in order, applying to the scalp a composition comprising at least one polyoxyethylenated sorbitan ester having less than or equal to 10 moles of ethylene oxide, and subsequently applying to the keratin fibers a dye composition comprising at least one dye precursor in a suitable medium. Such a process may make it possible to conserve strong a coloration while at the same time limiting the discomfort that may be experienced on the scalp at the time of application of the dye composition or after this application.

18 Claims, No Drawings

PROCESS FOR COLORING KERATIN FIBERS COMPRISING TREATING THE SCALP WITH AT LEAST ONE SORBITAN ESTER

CROSS-REFERENCE TO RELATED APPLICATIONS

This application claims benefit of U.S. Provisional Application No. 60/748,206, filed Dec. 8, 2005, the contents of which are incorporated herein by reference. This application also claims benefit of priority under 35 U.S.C. § 119 to French Patent Application No. FR 05 52494, filed Aug. 11, 2005, the contents of which are also incorporated herein by reference.

FIELD OF THE INVENTION

Disclosed herein is a process for dyeing keratin fibers, which comprises treating the scalp with at least one polyoxyethylenated sorbitan ester. BACKGROUND OF THE INVENTION It is known practice to dye keratin fibers, for example, human hair with dye compositions comprising oxidation dye precursors, which are generally known as oxidation bases, such as ortho- or para-phenylenediamines, ortho- or para-aminophenols, and heterocyclic compounds. These oxidation bases are colorless or weakly colored compounds, which, when combined with oxidizing products, can give rise to colored compounds via a process of oxidative condensation. The shades obtained with these oxidation bases may be modified by adding couplers or coloration modifiers, the latter being chosen, for example, from aromatic meta-diaminobenzenes, meta-aminophenols, meta-diphenols, and heterocyclic compounds such as indole and pyridine compounds.

Oxidation dyeing may be performed in the presence of an alkaline agent that promotes the dyeing of keratin fibers.

The variety of molecules used as oxidation bases and couplers allows a wide range of colors to be obtained. The "permanent" coloration obtained by means of these oxidation dyes may make it possible to obtain shades in the desired intensity and may show good fastness with respect to external agents such as light, bad weather, washing, permanent waving, perspiration, and/or rubbing.

However, since oxidation dyeing is performed in the presence of an oxidizing agent and an alkaline agent, it may lead to a sensation of discomfort reflected by local stinging and/or heating of the scalp.

It is known practice to protect keratin fibers that need to undergo or that have undergone a coloration using a dye precursor, for example, by using particular polymers. However, this protection is not entirely satisfactory: for instance, it may lead to less powerful dyeing due to the presence of these polymers.

Moreover, it is known practice to use polyoxyethylenated sorbitan esters in keratin fiber dyeing products. For example, German Patent No. 199 23 438 describes the use of polyoxyethylenated sorbitan esters to reduce the staining of the scalp during dyeing.

SUMMARY OF THE INVENTION

The present disclosure provides a novel process for dyeing keratin fibers, for instance, human keratin fibers such as the hair, which may limit the discomfort associated with dyeing.

DETAILED DESCRIPTION OF THE INVENTION

Thus, disclosed herein is a process for dyeing keratin fibers such as the hair, which comprises, in order, applying to the scalp a composition comprising at least one polyoxyethylenated sorbitan ester having less than or equal to 10 moles of ethylene oxide, and applying to the keratin fibers a dye composition comprising at least one dye precursor in a suitable medium.

Such a process may conserve strong coloration, while at the same time limiting the discomfort that may be experienced on the scalp at the time of application of the dye composition or after this application.

Examples of polyoxyethylenated sorbitan esters having less than or equal to 10 moles of ethylene oxide include sorbitan monolaurate oxyethylenated with 4 EO or polysorbate 21, sorbitan monostearate oxyethylenated with 4 EO or polysorbate 61, and sorbitan monooleate oxyethylenated with 5 EO or polysorbate 81. These sorbitan esters are sold, for example, by the company Uniqema under the names Tween 21, Tween 61, and Tween 81.

According to one embodiment, the number of moles of ethylene oxide may be less than 6 mol of ethylene oxide. In another embodiment, the number of moles of ethylene oxide may range from 2 to 5 mol of ethylene oxide.

According to the present disclosure, the at least one sorbitan ester may be present in the composition in a variable amount that depends, for example, on the type of coloration or the nature of the keratin fibers to be dyed. According to one embodiment, the at least one sorbitan ester may be present in the composition in an amount ranging from 0.01% to 20%, for example, from 0.1% to 10%, or from 1% to 8% by weight, relative to the total weight of the composition.

The composition in accordance with the present disclosure may further comprise at least one additive conventionally used in cosmetics, for example, in the field of hair dyeing. For instance, this composition may comprise antioxidants, penetrants, sequestrants, fragrances, buffers, dispersants, surfactants, conditioning agents, film-forming agents, thickeners, ceramides, preserving agents, nacreous agents, opacifiers, vitamins, and provitamins.

The composition may be in various forms such as lotions, gels, creams, shampoos, sticks, mousses, and sprays. The composition may be packaged in a pump-dispenser bottle or in an aerosol container. In the case of an aerosol, the composition may be combined with a propellant that may be chosen, for example, from alkanes, mixtures of alkanes, dimethyl ether, nitrogen, nitrous oxide, carbon dioxide, haloalkanes, and mixtures thereof.

The dye precursors that are suitable for use in the dye composition may include, for example, oxidation bases and couplers conventionally used for oxidation dyeing.

The oxidation bases may be chosen, for example, from para-phenylenediamines, bis(phenyl)alkylenediamines, para-aminophenols, bis-para-aminophenols, ortho-aminophenols, heterocyclic bases, and the addition salts thereof.

Non-limiting examples of para-phenylenediamines include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(o-hydroxyethyl)amino-2-chloroaniline, 2-β-hydroxyethylpara-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the acid addition salts thereof.

Suitable para-phenylenediamines include, for example, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid addition salts thereof.

Examples of bis(phenyl)alkylenediamines include, but are not limited to, N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the acid addition salts thereof.

Suitable para-aminophenols may include, for example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid addition salts thereof.

Non-limiting examples ortho-aminophenols include 2-aminophenol, 2-amino-5-methylphenol, 2-amino-6-methylphenol, 5-acetamido-2-aminophenol, and the acid addition salts thereof.

Heterocyclic bases may be chosen, for example, from pyridine derivatives, pyrimidine derivatives, and pyrazole derivatives.

Examples of pyridine derivatives include, for instance, the compounds described in British Patent Nos. 1 026 978 and 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine, 3,4-diaminopyridine, and the acid addition salts thereof.

Other examples of pyridine oxidation bases include, but are not limited to, 3-aminopyrazolo[1,5-a]pyridine oxidation bases and the addition salts thereof described, for example, in French Patent Application No. 2 801 308, such as pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2-(3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-ylpyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol; and the acid and base addition salts thereof.

Suitable pyrimidine derivatives include, for example, the compounds described in German Patent No. 2 359 399, Japanese Patent Application No. 88-169 571; Japanese Patent No. 05-63 124; European Patent No. 0 770 375, and International Patent Application Publication No. WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, and 2,5,6-triaminopyrimidine, and pyrazolopyrimidine derivatives such as those mentioned, for example, in French Patent Application No. 2 750 048, for example, pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropylaminopyrazolo[1,5-a]pyrimidine, the acid addition salts thereof, and the tautomeric forms thereof, when a tautomeric equilibrium exists.

Non-limiting examples of pyrazole derivatives include, for instance, the compounds described in German Patent Nos. 3 843 892 and 4 133 957, International Patent application Nos. WO 94/08969 and WO 94/08970, French Patent Application No. 2 733 749, and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the acid addition salts thereof.

The at least one oxidation base may be present in the dye composition in an amount ranging from 0.001% to 10% by weight, for each of them, relative to the total weight of the dye composition, for example, ranging from 0.005% to 6% by weight.

Couplers suitable for use in the dye composition may be chosen, for example, from meta-phenylenediamine couplers, meta-aminophenol couplers, meta-diphenol couplers, naphthalene-based couplers, heterocyclic couplers, and the addition salts thereof.

Examples of couplers include, but are not limited to, 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid addition salts thereof.

The at least one coupler may be present in the dye composition in an amount ranging from 0.001% to 10%, for each of them, for example, from 0.005% to 6% by weight, relative to the total weight of the dye composition.

The dye composition may also comprise direct dyes, which may be chosen, for example, from neutral, acidic, or cationic nitrobenzene direct dyes; neutral, acidic, or cationic azo direct dyes; neutral, acidic, or cationic quinone, for example, anthraquinone, direct dyes; azine direct dyes; triarylmethane direct dyes; indoamine direct dyes; and natural direct dyes.

The medium that is suitable for dyeing may be a cosmetic medium chosen from water and mixtures of water and at least one organic solvent, for instance branched or unbranched $C_1$-$C_4$ lower alcohols, such as ethanol and isopropanol; polyols and polyol ethers such as 2-butoxyethanol, propylene glycol, propylene glycol monomethyl ether, diethylene glycol monoethyl ether, and monomethyl ether; and glycerol; aromatic alcohols such as benzyl alcohol and phenoxyethanol; and mixtures thereof.

The at least one solvent may be present in the dye composition in an amount ranging from 1% to 40%, for example, from 5% to 30%, by weight relative to the total weight of the dye composition.

The dye composition may also comprise at least one adjuvant conventionally used in compositions for dyeing the hair, such as anionic, cationic, nonionic, amphoteric, or zwitterionic surfactants and mixtures thereof; anionic, cationic, nonionic, amphoteric, or zwitterionic polymers and mixtures thereof; inorganic or organic thickeners; antioxidants; penetrants; sequestrants; fragrances; buffers; dispersants; conditioning agents, for instance volatile or non-volatile, modified or unmodified silicones; film-forming agents such as nonionic, cationic, anionic, or amphoteric fixing polymers; preserving agents; and opacifiers.

The at least one adjuvant may be present in the dye composition in an amount ranging from 0.01% to 20% by weight, for each of them, relative to the total weight of the dye composition.

It is to be understood that a person skilled in the art will take care to select the at least one optional additional compound such that the advantageous properties intrinsically associated with the composition in accordance with the present disclosure are not, or are not substantially, adversely affected by the addition envisaged.

The pH of the dye composition in accordance with the present disclosure may range from 2 to 12, for example, from 6 to 12.

The pH may be adjusted to a desired value using acidifying or basifying agents conventionally used in the dyeing of keratin fibers, or alternatively, using standard buffer systems.

Examples of suitable acidifying agents include, but are not limited to, mineral and organic acids, such as hydrochloric acid, orthophosphoric acid, sulfuric acid, carboxylic acids, such as acetic acid, tartaric acid, citric acid, and lactic acid, and sulfonic acids.

Basifying agents may be chosen, for example, from aqueous ammonia, alkaline carbonates, alkanolamines such as mono-, di- and triethanolamine and derivatives thereof, sodium hydroxide, potassium hydroxide, and compounds of formula (III) below:

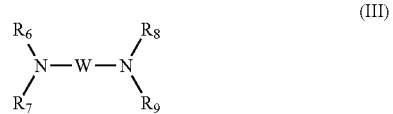

(III)

in which:

W is chosen from propylene residues optionally substituted with at least one entity chosen from hydroxyl groups and $C_1$-$C_4$ alkyl radicals; and $R_6$, $R_7$, $R_8$, and $R_9$, which may be identical or different, are chosen from hydrogen, $C_1$-$C_4$ alkyl radicals, and $C_1$-$C_4$ hydroxyalkyl radicals.

The dye composition may be used starting with a composition comprising at least one alkaline agent. The at least one alkaline agent may be present in the dye composition in an amount of greater than 5% by weight relative to the total weight of the dye composition, for example, greater than 10%, or greater than 15%, by weight relative to the total weight of the dye composition.

According to one embodiment of the present disclosure, the dye composition may comprise at least one basifying agent chosen, for example, from ammonia, alkanolamines such as ethanolamine, and/or silicates such as sodium silicate.

The dye composition according to the present disclosure may be in various forms, such as liquids, creams and gels, or any other form that is suitable for dyeing keratin fibers such as human hair.

The dye composition may also comprise at least one oxidizing agent. Non-limiting examples of oxidizing agents conventionally used for the oxidation dyeing of keratin fibers include hydrogen peroxide, urea peroxide, alkali metal bromates, persalts such as perborates and persulfates, peracids, and oxidase enzymes, for example peroxidases, 2-electron oxidoreductases such as uricases, and 4-electron oxygenases such as laccases. In at least one embodiment, the at least one oxidizing agent is hydrogen peroxide.

The at least one oxidizing agent may be added to the dye composition at the time of use, or it may be used starting with an oxidizing composition containing it, this composition being applied simultaneously with or sequentially to the composition of the present disclosure. The oxidizing composition may also comprise at least one adjuvant conventionally used in hair dye compositions and as defined above.

The pH of the oxidizing composition comprising the at least one oxidizing agent may be such that, after mixing with the dye composition, the pH of the resulting composition applied to the keratin fibers ranges from 3 to 12, for example, from 6 to 12. The pH may be adjusted to the desired value by means of acidifying or basifying agents conventionally used in the dyeing of keratin fibers and as defined above.

The dye composition that is finally applied to the keratin fibers may be in various forms, such as liquids, creams, and gels, or any other form that is suitable for dyeing keratin fibers such as human hair.

According to one embodiment of the present disclosure, the leave-on time for the composition comprising the sorbitan ester may range from a few seconds, for example 5 seconds, to 60 minutes, for example, from 30 seconds to 45 minutes.

The treatment step using the composition comprising the sorbitan ester may be performed at a temperature ranging, for example, from 10° C. to 220° C., for instance, from 10° C. to 70° C., from 10 to 60° C., or at room temperature.

The step of treating the fibers using the composition comprising the sorbitan ester may be followed by a step of rinsing before applying the dye composition. However, according to one embodiment, the application of the composition comprising the sorbitan ester is not followed by rinsing before the application of the dye composition.

The dyeing step may be performed conventionally for a time that is sufficient to obtain the desired coloration. The leave-on time may range from 1 to 60 minutes, for example, from 5 to 60 minutes. The dyeing step may be followed by a rinsing step.

The treatment step using the sorbitan ester and/or the dyeing step of the process of the present disclosure may be performed at room temperature or at higher temperatures, for example using a hairdryer, a drying hood, and/or a smoothing iron, etc.

In at least one embodiment, the step of applying the dye composition may take place immediately after applying the sorbitan ester. The two applications may, however, be staggered over time, and in at least one embodiment, the staggering may be up to 30 minutes. According to another embodiment, this staggering may range from 30 seconds to 15 minutes.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

The treatment compositions described in Table 1 below were prepared. All quantities are expressed in grams, unless otherwise indicated.

TABLE 1

|  | A | B |
|---|---|---|
| Chlorhexidine hydrochloride | 0.02 | |
| Methyl p-hydroxybenzoate | 0.2 | |
| Microbiologically clean deionized water | 88.28 | |
| Cetylstearyl alcohol (30/70 C16/C18) | 6 | |
| Oxyethylenated cetylstearyl alcohol (33 EO) | 1.5 | |
| Oxyethylenated sorbitan monolaurate (4 EO) | 4 | 100 |

Each of these compositions was applied to the scalp in an amount sufficient to protect the scalp. This application was followed by applying a dye composition chosen from compositions 1-4 as described below in Tables 2 and 3.

TABLE 2

|  | Composition 1 | Composition 2 |
|---|---|---|
| 1-Methyl-2,5-diaminobenzene | 1.7 g | 0.5 g |
| 1-Hydroxy-4-aminobenzene | | 0.4 g |
| 1,3-Dihydroxybenzene | 1 g | 0.25 g |
| 1-Hydroxy-3-aminobenzene | 0.07 g | |
| 1-β-Hydroxyethyloxy-2,4-diaminobenzene dihydrochloride | 0.03 g | |
| 2-Methyl-1,3-dihydroxybenzene | 0.5 g | 0.3 g |
| 1-Methyl-2-hydroxy-4-aminobenzene | | 0.25 g |
| 1-Methyl-2-hydroxy-4-β-hydroxyethyl-aminobenzene | | 0.05 g |
| 6-Hydroxyindole | | 0.01 g |
| Pure monoethanolamine | 5 g | |
| Aqueous ammonia containing 20% $NH_3$ | | 15 g |
| Polyquaternium-6 sold by Nalco | | 3 g |
| Polyquaternium-22 sold by Nalco | 1.5 g | |
| Hexadimethrine chloride (Mexomere PO, Chimex) | 1.5 g | |
| Propylene glycol | 10 g | 10 g |
| Carbopol 980 sold by Noveon (crosslinked polyacrylic acid) | 0.4 g | 0.4 g |
| Lauryl alcohol oxyethylenated with 12 mol of ethylene oxide | 7.5 g | 7.5 g |
| Oleocetyl alcohol oxyethylenated with 30 mol of EO | 6 g | 6 g |
| Decyl alcohol oxyethylenated with 3 mol of EO | 8 g | 8 g |
| Lauric acid | 2.5 g | 2.5 g |
| 50/50 Cetylstearyl alcohol | 10 g | 10 g |
| Hydrophobic fumed silica | 1 g | 1 g |
| Glyceryl monostearate | 1 g | 1 g |
| Reducing agent, antioxidant, sequestrant, fragrance | qs | qs |
| Demineralized water qs | 100 g | 100 g |

TABLE 3

|  | Composition 3 | Composition 4 |
|---|---|---|
| 1-Methyl-2,5-diaminobenzene | 1.7 g | 0.007 g |
| 1-Hydroxy-4-aminobenzene | | 0.007 g |
| 1,3-Dihydroxybenzene | 1 g | 0.014 g |
| 1-Hydroxy-3-aminobenzene | 0.07 g | |
| 1-β-Hydroxyethyloxy-2,4-diaminobenzene dihydrochloride | 0.03 g | |
| 2-Methyl-1,3-dihydroxybenzene | 0.5 g | |
| Aqueous ammonia containing 20% $NH_3$ | 10 g | 20 g |
| Polyquaternium-6 sold by Nalco | | 3 g |
| Polyquaternium-22 sold by Nalco | 1.5 g | |
| Hexadimethrine chloride (Mexomere PO, Chimex) | 1.5 g | |

TABLE 3-continued

|  | Composition 3 | Composition 4 |
|---|---|---|
| Oleic acid | 2.5 g | 2.5 g |
| Mixture of stearyl alcohols more or less oxyethylenated (2 to 21 EO) | 15 g | 15 g |
| Oleyl alcohol | 1 g | 1 g |
| Monamid 972 sold by Uniqema (fatty amide) | 3 g | 5 g |
| Glycerol |  | 5 g |
| Polyurethane-16 | 0.2 g | 0.4 g |
| Hydroxypropylmethylcellulose | 0.3 g | 0.7 g |
| Reducing agent, antioxidant, sequestrant, fragrance | qs | qs |
| Demineralized water qs | 100 g | 100 g |

The dye compositions 1 to 4 were mixed extemporaneously with aqueous hydrogen peroxide solution under the conditions described below:

Composition 1: mixing with one and a half times their volume of 9-volumes aqueous hydrogen peroxide solution;

Compositions 2 and 3: mixing with one and a half times their volume of 20-volumes aqueous hydrogen peroxide solution;

Composition 4: mixing with twice their volume of 40-volumes aqueous hydrogen peroxide solution.

The mixtures thus prepared were applied to natural grey hair containing 90% white hairs, at a rate of 30 g per 3 g of hair.

After a leave-on time of 30 minutes, the hair was rinsed, washed with a standard shampoo, and then rinsed again.

The hair coloration was evaluated visually. The results are presented in Table 4 below:

TABLE 4

|  | Tone depth | Tint |
|---|---|---|
| Composition 1 | Chestnut | Natural |
| Composition 2 | Dark blond | Mahogany coppery |
| Composition 3 | Chestnut | Natural |
| Composition 4 | Very very light blond | Natural |

The fibers thus obtained showed a satisfactory coloration under comfortable conditions for the model.

What is claimed is:

1. A process for dyeing keratin fibers, comprising, in order, applying to the scalp a treatment composition comprising at least one polyoxyethylenated sorbitan ester having less than or equal to 10 moles of ethylene oxide, and applying to the fibers a dye composition comprising at least one dye precursor in a suitable medium.

2. The process according to claim 1, wherein the at least one polyoxyethylenated sorbitan ester is chosen from polyoxyethylenated sorbitan esters having less than 6 moles of ethylene oxide.

3. The process according to claim 1, wherein the at least one polyoxyethylenated sorbitan ester is chosen from polyoxyethylenated sorbitan esters having from 2 to 5 moles of ethylene oxide.

4. The process according to claim 1, wherein the at least one polyoxyethylenated sorbitan ester is chosen from sorbitan monolaurate oxyethylenated with 4 EO, sorbitan monostearate oxyethylenated with 4 EO, and sorbitan monooleate oxyethylenated with 5 EO.

5. The process according to claim 1, wherein the at least one polyoxyethylenated sorbitan ester is present in the treatment composition in an amount ranging from 0.01% to 20% by weight relative to the total weight of the treatment composition.

6. The process according to claim 5, wherein the at least one polyoxyethylenated sorbitan ester is present in the treatment composition in an amount ranging from 0.1% to 10% by weight relative to the total weight of the treatment composition.

7. The process according to claim 6, wherein the at least one polyoxyethylenated sorbitan ester is present in the treatment composition in an amount ranging from 1% to 8% by weight relative to the total weight of the treatment composition.

8. The process according to claim 1, wherein the treatment composition further comprises at least one adjuvant chosen from antioxidants, penetrants, sequestrants, fragrances, buffers, dispersants, surfactants, conditioning agents, film-forming agents, thickeners, preserving agents, nacreous agents, and opacifiers.

9. The process according to claim 1, wherein the dye composition comprises at least one oxidation base chosen from para-phenylenediamines, bis(phenyl)alkylenediamines, para-aminophenols, bis-para-aminophenols, ortho-aminophenols, heterocyclic bases, and the addition salts thereof.

10. The process according to claim 9, wherein the at least one oxidation base is present in the dye composition in an amount, for each of them, ranging from 0.001% to 10% by weight relative to the total weight of the dye composition.

11. The process according to claim 10, wherein the at least one oxidation base is present in the dye composition in an amount, for each of them, ranging from 0.005% to 6% by weight relative to the total weight of the dye composition.

12. The process of claim 1, wherein the dye composition comprises at least one coupler chosen from meta-phenylenediamine couplers, meta-aminophenol couplers, meta-diphenol couplers, naphthalene-based couplers, heterocyclic couplers, and the addition salts thereof.

13. The process according to claim 12, wherein the at least one coupler is present in the dye composition in an amount, for each of them, ranging from 0.001% to 10% by weight relative to the total weight of the dye composition.

14. The process according to claim 13, wherein the at least one coupler is present in the dye composition in an amount, for each of them, ranging from 0.005% to 6% by weight relative to the total weight of the dye composition.

15. The process according to claim 14, wherein the dye composition further comprises at least one direct dye.

16. The process according to claim 1, wherein the treatment composition is left on the scalp for a leave-on time ranging from 5 seconds to 60 minutes.

17. The process according to claim 1, wherein the dye composition is left on the keratin fibers for a leave-on time ranging from 1 minute to 60 minutes.

18. The process according to claim 1, wherein which the dye composition comprises at least one basifying agent.

* * * * *